United States Patent
Brinks et al.

(10) Patent No.: US 8,989,845 B2
(45) Date of Patent: Mar. 24, 2015

(54) MODEL-BASED EXTENSION OF FIELD-OF-VIEW IN NUCLEAR IMAGING

(75) Inventors: Ralph Brinks, Hagen (DE); Eike G. Gegenmantel, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 241 days.

(21) Appl. No.: 13/146,664

(22) PCT Filed: Jan. 12, 2010

(86) PCT No.: PCT/IB2010/050106
§ 371 (c)(1),
(2), (4) Date: Jul. 28, 2011

(87) PCT Pub. No.: WO2010/095062
PCT Pub. Date: Aug. 26, 2010

(65) Prior Publication Data
US 2011/0288407 A1    Nov. 24, 2011

Related U.S. Application Data

(60) Provisional application No. 61/152,981, filed on Feb. 17, 2009.

(51) Int. Cl.
*A61B 6/03* (2006.01)
*A61B 6/00* (2006.01)

(52) U.S. Cl.
CPC .............. *A61B 6/032* (2013.01); *A61B 6/037* (2013.01); *A61B 6/5235* (2013.01)
USPC ........... 600/427; 600/425; 600/436; 600/407; 378/4

(58) Field of Classification Search
CPC combination set(s) only.
See application file for complete search history.

(56) References Cited

U.S. PATENT DOCUMENTS

| | | |
|---|---|---|
| 6,490,476 B1 | 12/2002 | Townsend et al. |
| 7,813,783 B2 | 10/2010 | Thomas et al. |

(Continued)

FOREIGN PATENT DOCUMENTS

| | | |
|---|---|---|
| EP | 1891899 A1 | 2/2008 |
| JP | 2004237076 A | 8/2004 |
| JP | 2008-194292 A | 8/2008 |

OTHER PUBLICATIONS

Sureshbabu et al.,"PET/CT Imaging Artifacts", Journal of Nuclear Medicine Technology, 2005, 33:156-161.*

(Continued)

*Primary Examiner* — Long V Le
*Assistant Examiner* — Farshad Negarestan

(57) ABSTRACT

A CT imaging system (12) generates structural data of a first FOV which is reconstructed by a CT reconstruction processor (52) into a CT image representation. A nuclear imaging system acquires functional data from a second FOV which is smaller than the first FOV. A first PET reconstruction processor (60) reconstructs the functional data into a PET image representation. A fusion processor (64) combines the PET image representation with a map extracted from the CT image representation to generate an extended FOV image representation. A spill-over correction unit (66) and a backscatter correction unit (68) derive spill-over correction data and backscatter correction data from the extended FOV image representation. A reconstruction processor (70) generates a spill-over and backscatter corrected functional image representation based on the spill-over correction data, the backscatter correction data, and the functional data.

19 Claims, 6 Drawing Sheets

(56) References Cited

U.S. PATENT DOCUMENTS

2008/0073543 A1    3/2008  Vija et al.
2008/0187094 A1*   8/2008  Stodilka et al. .................. 378/22

OTHER PUBLICATIONS

Boussion, N., et al.; A multiresolution image based approach for correction of partial volume effects in emission tomography; 2006; Phys. Med. Biol.; 51:abstract.

Dekemp, R. A., et al.; Will 3-dimensional PET-CT enable the routine quantification of myocardial blood flow?; 2007; Journal of Nuclear Cardiology; 14(3)abstract.

Rousset, O. G., et al.; Correction for Partial Volume Effects in PET: Principle and Validation; 1998; J. of Nuclear Medicine; 39(5)904-911.

Willowson, K., et al.; Transmission dependent scatter correction: CT based corrections for quantitative SPECT; 2007; Aust. Phy. & Eng. Sci.; 30(1)abstract.

Willowson, K., et al.; Quantitative SPECT reconstruction using CT-derived corrections; 2008; Phys. Med. Biol.; 53:3099-3112.

* cited by examiner

MODEL-BASED EXTENSION OF FIELD-OF-VIEW IN NUCLEAR IMAGING

CROSS REFERENCE TO RELATED APPLICATIONS

This application claims the benefit of U.S. provisional application Ser. No. 61/152,981 filed Feb. 17, 2009, which is incorporated herein by reference.

The present application relates to the medical imaging systems and methods. It finds particular application in conjunction with multi-modal systems, such as PET/CT systems. It will be appreciated that the invention is also applicable to the various combinations of SPECT, CT, PET, MRI, and the like.

In multi-modal tomographic systems, two or more different imaging modalities are used to locate or measure different constituents in the object space. In the PET/CT system, the PET imaging system creates images of high metabolic activity in the body, rather than creating images of surrounding anatomy. CT scans allow doctors to see the internal structures within the human body. Before having a PET/CT scan, the patient receives a dose of a radiopharmaceutical. The pharmaceutical is carried through the blood and concentrates in one or more target organs or regions and causes annihilation events which emit positrons. During the scan, tracings of the emitted radiation are detected by the system creating an image of the distribution of the radiopharmaceutical in the patient. The image can show the circulatory system and/or the relative absorption of the radiopharmaceutical in various regions or organs. Integration of the anatomical data from the CT scan with the metabolic data from the PET scan in the PET/CT image gives physicians visual information to determine if disease is present, the location and extent of disease, and track how rapidly it is spreading. The PET/CT system is particularly helpful in difficult-to-treat regions (e.g. head and neck area, mediastinum, postsurgical abdomen) and localization of the treatment area for the patients receiving radiation therapy or chemotherapy.

The CT scan data can be used for attenuation correction further enhancing PET images. Attenuation correction in traditional PET systems can involve a transmission scan in which an external radioactive transmission source rotates around the FOV and measures the attenuation through the examination region in two scenarios in which the patient is absent and then patient is present in the examination region. The ratio of the two values is used to correct for non-uniform densities which can cause image noise, image artifacts, image distortion, and can mask vital features.

The PET/CT systems use the CT transmission data to construct an attenuation map of density differences throughout the body and used to correct for absorption of emitted photons. CT based attenuation correction benefits from low statistical noise, high speed acquisition, immunity from injected radioisotope related interference, and the elimination of radioactive transmission source hardware.

Scatter correction algorithms can also benefit from a CT derived attenuation map. Scatter correction algorithms model scatter distribution based on the CT transmission attenuation map and the emission PET data. After the scatter contribution is subtracted, the PET data is reconstructed to yield scatter corrected images.

Cardiac studies using nuclear imaging are common Coronary perfusion and myocardial viability studies are usually performed by SPECT, but PET is gaining because attenuation interference caused by the chest and diaphragm can be easily corrected with transmission scan based attenuation maps.

Both nuclear imaging modalities suffer from a limited field of view (FOV) which is especially true for dynamic heart studies using PET, where data is acquired in only one bed position. A limited spatial resolution makes scatter estimates and spill-over estimate of activity outside the FOV difficult because this activity outside the FOV is not measured. For example, in cardiac studies the liver, which is in close proximity to the heart, takes up large amounts of the radioactive tracer and creates a spill-over of activity in the heart region. In whole body studies, spill-over can be corrected using partial volume correction algorithms; however, a problem occurs when the source of spill-over activity is partially or completely excluded from the FOV. In addition, backscatter from the liver outside the FOV cannot be modeled in a single scatter simulation (SSS).

The present application provides a new and improved diagnostic imaging system that is capable of quantifying a significant amount of activity outside the nuclear imaging FOV which overcomes the above-referenced problems and others.

In accordance with one aspect, a combined imaging system is provided which is comprised of a first imaging system and a nuclear imaging system. The first imaging system is configured to acquire structural data of at least one anatomical structure in a first FOV. The nuclear imaging system is configured to acquire functional data of at least one anatomical structure in a second FOV, wherein the second FOV is smaller than the first FOV. A reconstruction processor is configured to reconstruct the functional data acquired by the nuclear imaging system corrected for at least one of spill-over and backscatter artifacts based on the structural data acquired by the first imaging system.

In accordance with another aspect, a method is provided for using a combined imaging system which includes acquiring structural data of at least one anatomical structure in a first FOV with a first imaging system. Functional data of at least one anatomical structure in a second FOV is acquired by a nuclear imaging system, wherein the second FOV is smaller than the first FOV. The functional data is corrected for at least one of spill-over and backscatter artifacts based on the structural data acquired by the first imaging system and reconstructed.

One advantage is that higher signal-to-noise ratios can be realized in functional PET images.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
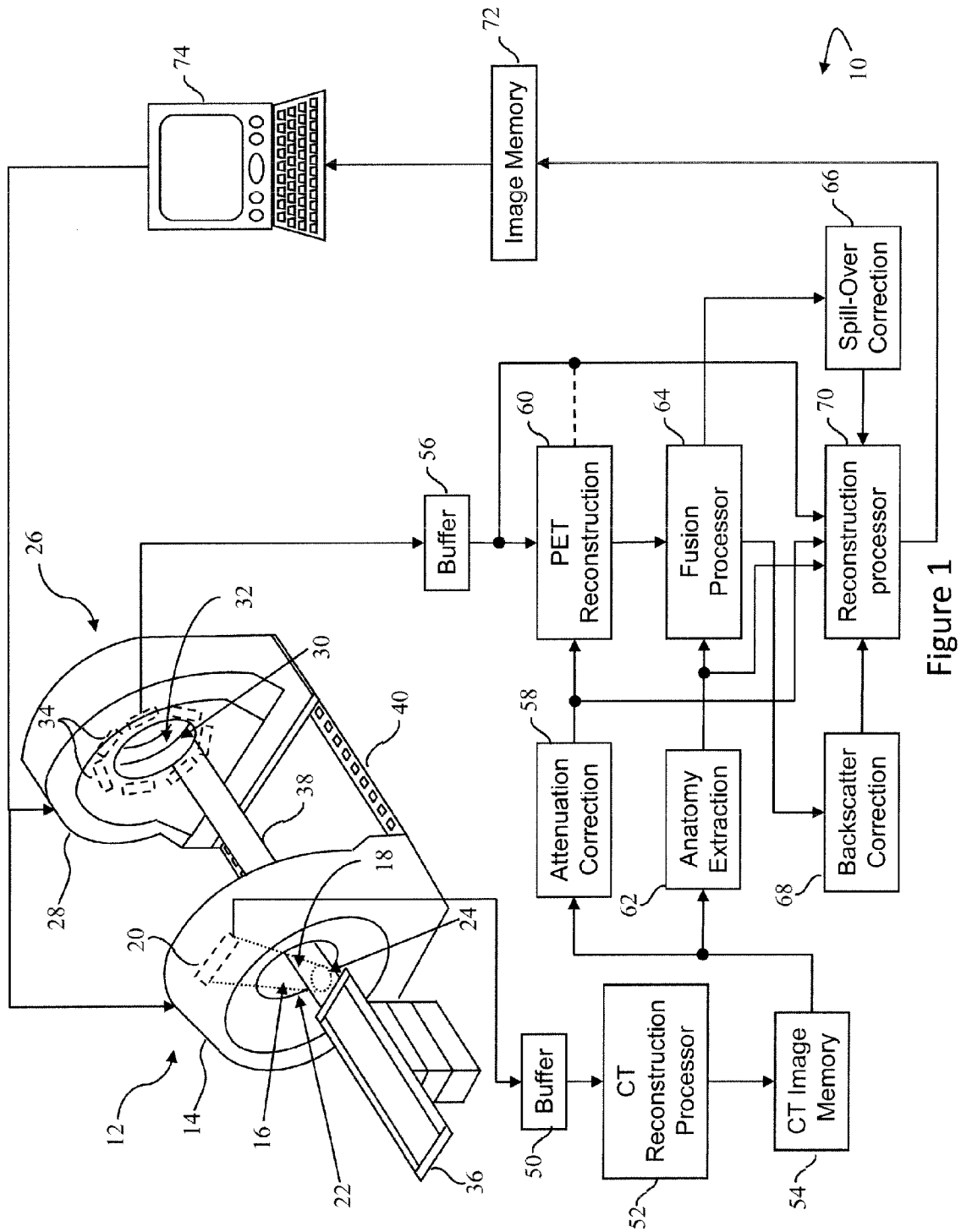
FIG. 1 is a diagrammatic view of combined PET/CT system with model based extension of the FOV.

With reference to FIG. 1, a diagnostic imaging system 10 is capable of x-ray computer tomography (CT) and nuclear imaging, such as PET or SPECT. The diagnostic imaging system 10 includes a first imaging system, in the illustrated embodiment a CT scanner 12, housed within a first gantry 14. A bore 16 defines a first examination region 18 of the CT scanner 12. An array of radiation detectors 20 is disposed on a rotating gantry 22 configured to receive transmission radiation from an x-ray source 24 disposed opposite the detectors 20 on the rotating gantry 22. It should be appreciated that other imaging modalities are also contemplated.

A second imaging system, in the illustrated embodiment a PET scanner 26, is housed within a second gantry 28 which defines a patient receiving bore 30. It should be appreciated that SPECT or other imaging modalities are also contemplated. A stationary ring of radiation detectors 34 are arranged around the bore 30 to define a second or PET examination region 32.

The two gantries 14, 28 are adjacent to one another and share a common patient support 36 that translates along a longitudinal axis between the two examination regions 18, 32 along a patient support track or path 38. A motor or other drive mechanism (not shown) provides the longitudinal movement and vertical adjustments of the support in the examination regions 18, 32. In the illustrated embodiment, the PET gantry 28 translates along a gantry track 40 to reduce the transit time between imaging systems 12, 26. A closed arrangement between gantries reduces the likelihood of patient movement and misregistration errors stemming from increased scan times. Mounting the CT and PET systems in a single, shared gantry with a common examination region is also contemplated.

Figure 2:
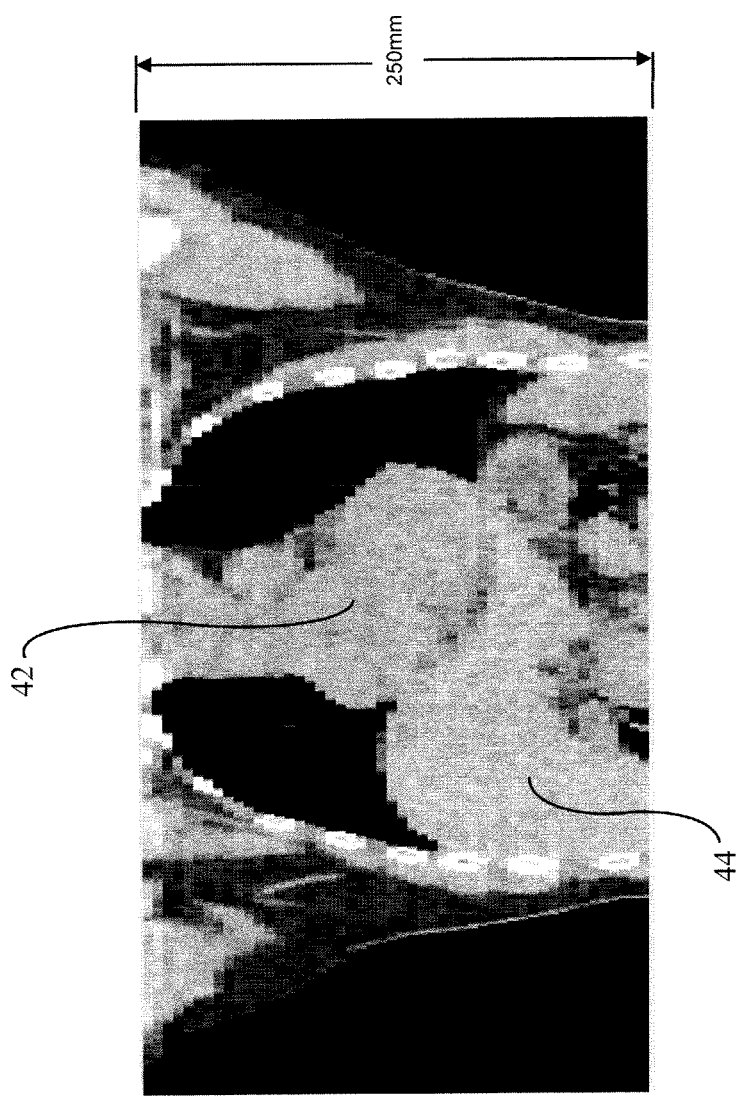
FIG. 2 is a CT surview scan in which the entire liver in the FOV.

With continuing reference to FIG. 1, the patient support 36 positions the patient or subject to be imaged into the first examination region 18 for a CT surview scan to be generated by the CT scanner 12. In a cardiac study, the surview scan is approximately 250 mm in the axial direction and encompasses the thorax to include the heart 42 and the liver 44. The acquired surview data is stored in a data buffer 50 and processed by CT reconstruction processor 52 into a CT image representation (FIG. 2) and then stored in a CT image memory unit 54.

The patient support moves the subject to the PET examination region 32. With respect to a cardiac study, the patient support aligns the subject's heart within the PET FOV, typically 180 mm in diameter cylinder, based on the CT surview scan. The acquired PET data is stored in a data buffer 56.

An attenuation map is generated by an attenuation correction unit 58 which is used by a PET image reconstruction processor 60 to generate an attenuation corrected PET image representation (FIG. 3) from the PET data. An anatomy map is generated by the anatomy extraction unit 62 which extracts the anatomical shape or outlines of the organ(s) of interest outside the FOV using techniques such as segmentation, principal components analysis, or the like. In a cardiac study, the anatomical shape of the liver or other high activity organs is modeled by the anatomy extraction unit 62 and used to extend the effective FOV of a PET image representation for image correction purposes. A fusion processor 64 aligns, registers, or fuses the attenuation correction PET image representation and the anatomy map and extrapolates PET image intensity values to the extracted organs, outside of the actual PET FOV to generate a theoretical extension of the PET FOV (FIG. 4). The extended FOV PET data is used by a spill-over correction unit 66 and a scatter simulation unit 68 to create corrected data sets to be used by a reconstruction processor 70 that generates a corrected PET image representation that is later stored in an image memory unit 72.

Figure 3:
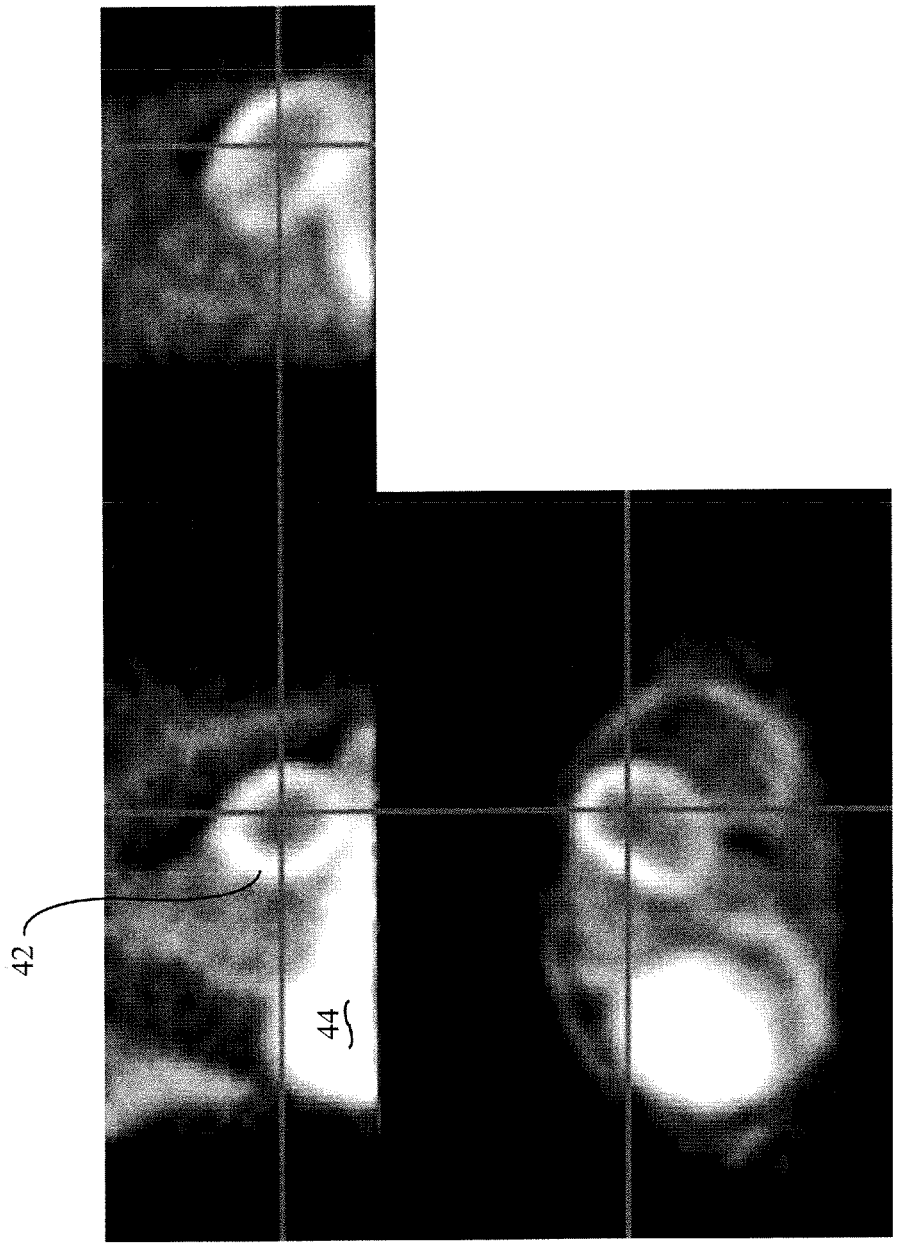
FIG. 3 illustrates three views of a patient during dynamic perfusion study with $NH_3$.
Figure 4:
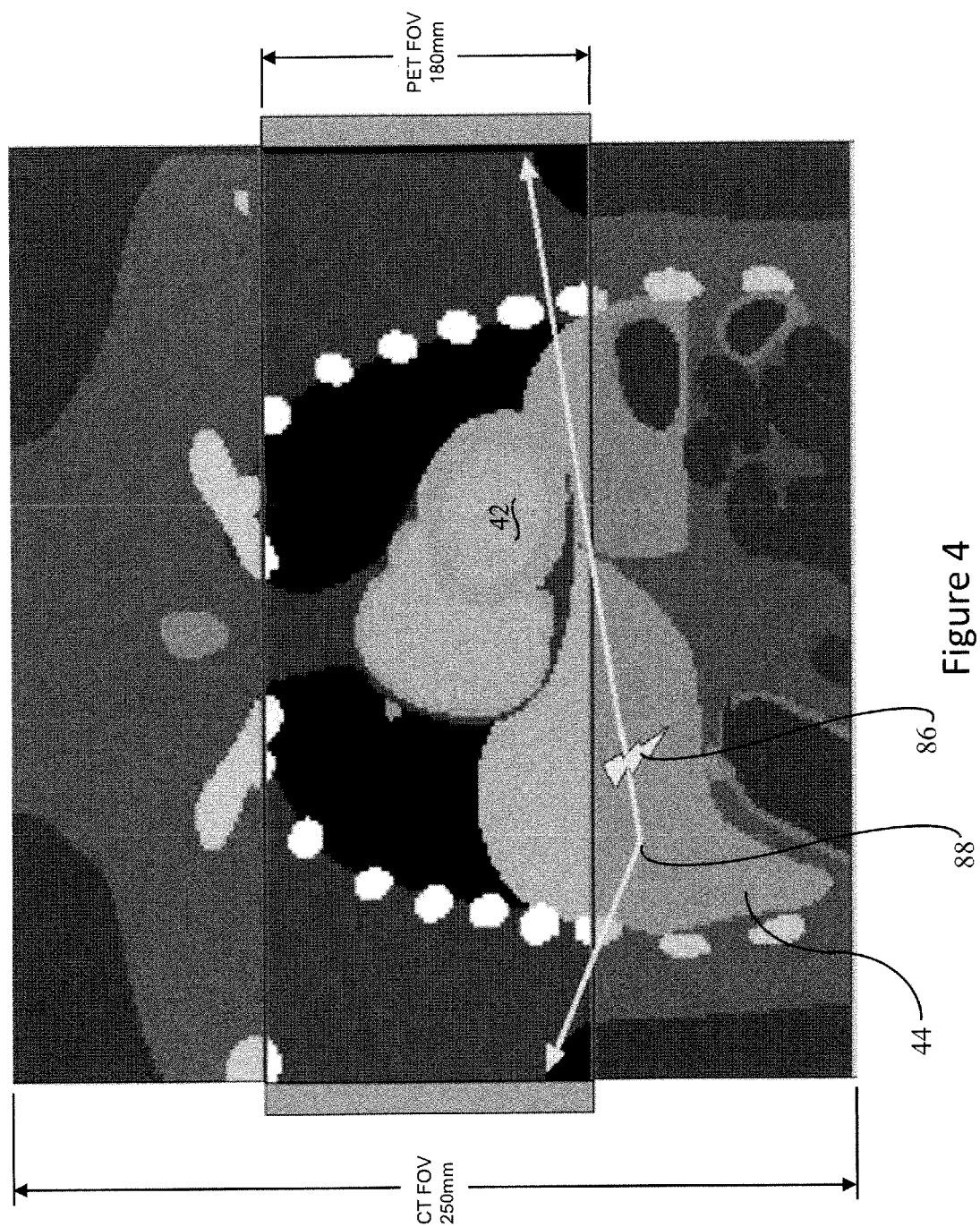
FIG. 4 is an illustration of a backscatter event outside the FOV that yields a false coincidence event in nuclear detectors.

Unlike the PET image of FIG. 3 in which the liver 44 is truncated, in the fusion image of FIG. 4, the entire liver is illustrated. The entire liver is assigned the same intensity value as is found in the portion of the liver found in the PET image of FIG. 3. Other organs with significant tracer compensations may be treated similarly. The fusion image then functions as an extended PET image in which the liver is not truncated. The expanded image of FIG. 4 is then used by the spill-over correction unit 66 and the scatter simulation unit 68 to create the spill-over and scatter corrections. The spill-over and scatter correction can be performed either on the projection data from the buffer 56, or can be performed on the attenuation corrected image from the PET reconstruction processor 60.

Reconstructed corrected PET image representations, fused PET and CT images, and others, are displayed on a graphic user interface 74. The graphic user interface 74 also includes a user input device which a clinician can use for controlling the imaging system to select scanning sequences and protocols, fused image combinations, and the like. The graphic user interface also displays the pre-corrected and corrected images concurrently for verification and/or further manual correction.

Any real imaging device has a limited spatial resolution which can be described in terms of the full width at half maximum (FWHM) of an image of a point source. Limited resolution implies a phenomenon that is termed "spill-out effect". In the final image, this results in activity being assigned to regions without activity.

Figure 5:
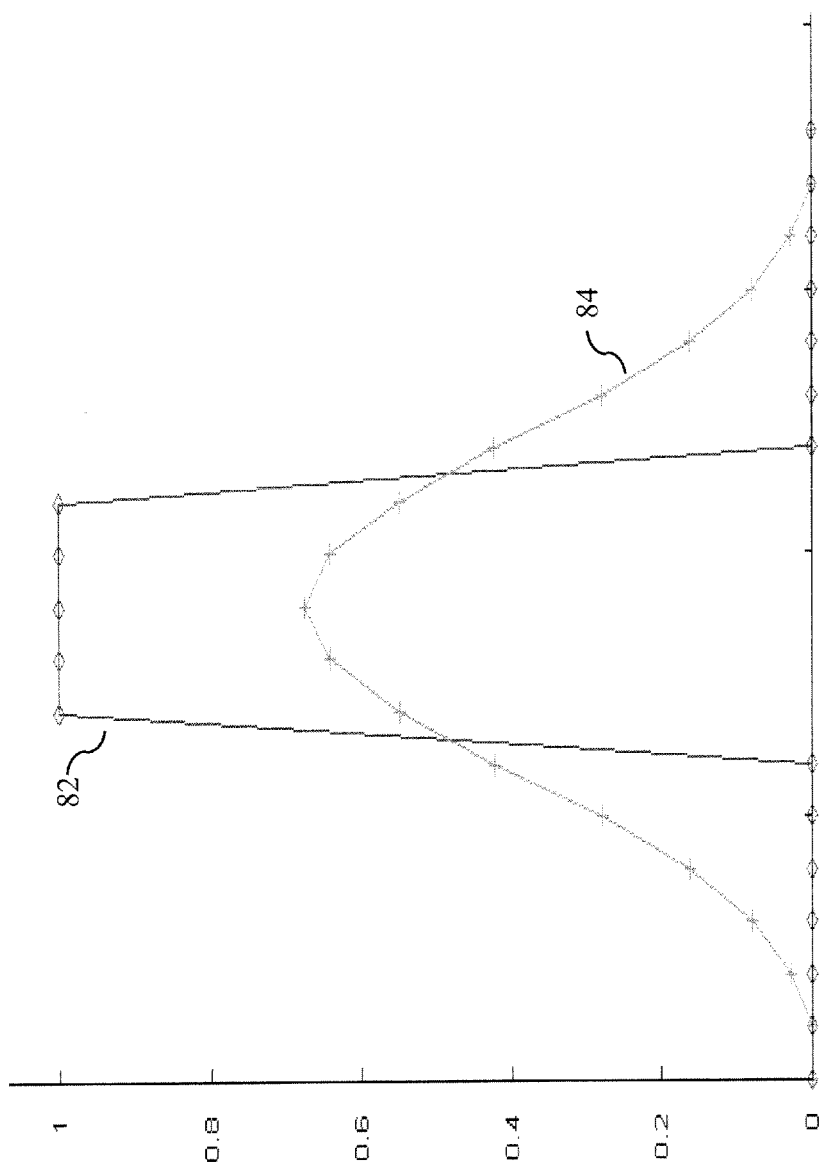
FIG. 5 is a graph that quantifies spill-out activity. A region with homogenous activity ($\Diamond$) is represented in an image as a smoothed profile (+).

With reference to FIG. 5, when a region 82 with high activity is close to another region, some of the activity spills-over 84 into adjoining regions. The spill-over 84 can be modeled if the region 82 is in the field-of-view. In the example of the liver and the heart, the liver is effectively in the field-of-view in the fused image of FIG. 4. Spill-over correction algorithms when the entire contributing organ is in the field-of-view are known in the art.

Spill-over from partial volume effects takes place between objects with approximately less than 3 times the FWHM of the imaging system. Currently, FWHMs are in the range of about 6-7 mm for PET, and more for SPECT. By way of example, the diaphragm separates the liver and the pericardium, the sack that contains the heart. The diaphragm has a thickness of less than 5 mm and the pericardium has an approximate thickness of 1 mm; consequently, spill over from the liver to the heart will take place because they are separated by approximately 5 mm.

Looking again to FIG. 4, a radiation event 86 may be scattered 88 outside of the field-of-view by Compton scatter. If the unscattered γ-ray from the PET event and the scattered γ-ray are both detected in the field-of-view, this can appear as a normal PET event occurring on the line between the two detection points. Backscattering can be modeled, as is known in the art. However, the modeling requires a knowledge of the structure which is scattering the γ-ray. When this structure is outside of the field-of-view, the structure cannot be modeled. Again, using the fused image of FIG. 4, structures outside the PET field-of-view is known, enabling the modeling algorithms to work.

Figure 6:
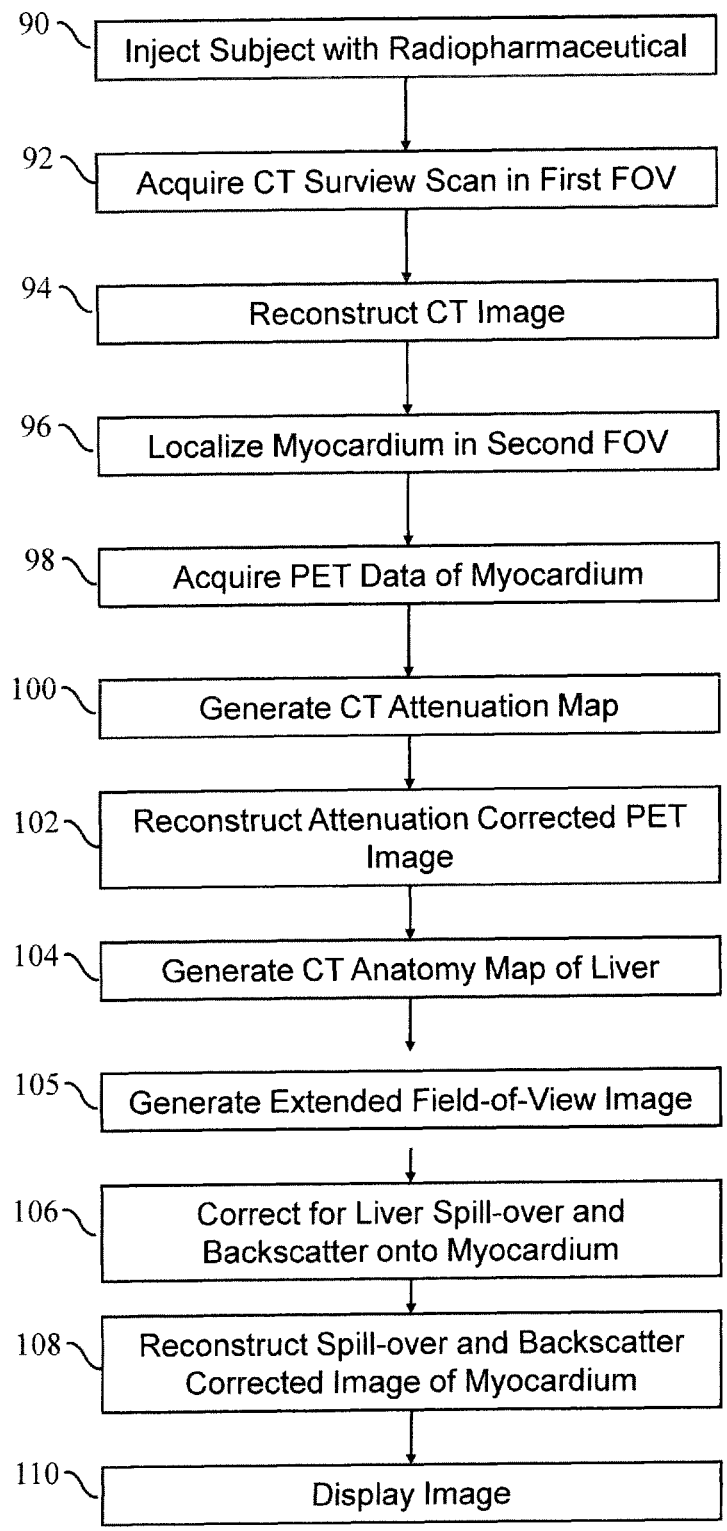
FIG. 6 illustrates a flowchart diagram of a method for model based extension of FOV.

With reference to FIG. 6, in PET cardiac studies, e.g. perfusion or viability studies, the liver takes up large amounts of the radiopharmaceutical. Due to the limited FOV of PET, significant spill over from the liver to the heart can occur. The subject is then injected with a radiopharmaceutical 90 such as FDG, ammonia, or the like. After an uptake period, the subject is positioned in the CT scanner and a low dose surview scan of the entire heart and liver is acquired 92 then the image data is reconstructed into image representations 94 using known methods. The CT images representations are used to align the heart to the PET FOV 96. The subject heart is then positioned in the PET FOV and PET data of the entire heart and partially excluded liver is acquired 98. The CT image representations are used to determine attenuation correction factors that are arranged to generate an attenuation map 100 that is used to reconstruct an attenuation corrected PET image representation 102. In a separate process, the anatomical shape of the liver is extracted from the CT image representations. An anatomy map of the liver is generated 104 by scaling the anatomical liver representation to match the emission energy of the PET scanner and by assigning the liver radiopharmaceutical activity. The liver activity can be assigned based on the activity of the partially excluded liver from the attenuation corrected PET image representation or using an estimated value. Assuming the liver has uniform uptake, the PET FOV can be theoretically extended using the anatomy map. An extended FOV image representation is generated by registering then combining the anatomy map of the liver and the attenuation corrected PET image representation of the heart. Known spill-over and scatter correction methods are applied 106 to the extended FOV image representation and the corrected image representations are then reconstructed 108. In another embodiment, the anatomical shape of the partially excluded liver can be extracted from attenuation corrected images. The partial anatomical shape can be correlated with a database or a model to estimate the remaining shape of the liver. The estimated anatomical shape of the liver is then scaled and combined with an attenuation corrected PET image representation and then corrected for spill-over and scatter.

In another embodiment, if non-uniform uptake is assumed in an anatomical structure that is partially excluded from the PET FOV, then scatter correction and spill-over correction can be applied during PET image reconstruction based on the partial anatomical structure within the PET FOV.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A combined imaging system comprising:
    a first imaging system configured to acquire structural data of at least one anatomical structure in a first field-of-view (FOV);
    a first imaging system reconstruction processor configured to reconstruct the acquired structural data from the first imaging system into a first system image representation;
    a nuclear imaging system configured to acquire functional data of the at least one anatomical structure in a second FOV, the second FOV being smaller than the first FOV such that the first FOV includes data excluded from the second FOV; and
    one or more processors configured to:
        extract from the first system image representation a first map including at least a first portion of at least one anatomical structure excluded from the second FOV and included in the first FOV;
        generate an attenuation map based on the first system image representation;
        process the functional data into an attenuation corrected image representation based on the attenuation map;
        align, register, or fuse the attenuation corrected image representation and the first map and extrapolate nuclear image intensity values to at least the first portion of the at least one anatomical structure excluded from the second FOV and included in the first FOV based on nuclear image intensity values of a second portion of the at least one anatomical structure included in the second FOV to generate an extended FOV image representation; and
        reconstruct the extended FOV image representation into a corrected nuclear image representation.

2. The combined imaging system according to claim 1, wherein the extended FOV image representation is corrected for at least one of spill-over and backscatter artifacts based on the structural data.

3. The combined imaging system according to claim 2, wherein the first imaging system is a CT imaging system and the structural data is acquired during a surview scan.

4. The combined imaging system according to claim 2, wherein the first FOV encompasses the second FOV.

5. The combined imaging system according to claim 1, wherein the one or more processors are further configured to generate:
    scatter correction data based on a scatter simulation derived from the extended FOV image representation; and
    spill-over correction data based on the extended FOV image representation; and
    wherein the correction data is used to correct at least one of spill-over and backscatter artifacts when the extended FOV image representation is reconstructed into the corrected nuclear image representation.

6. The imaging system according to claim 5, further including a user interface including a display which displays pre-corrected and corrected nuclear image representation concurrently for verification and manual correction.

7. A method of combined imaging, comprising:
    acquiring structural data of at least one anatomical structure in a first field of view with a first imaging system;
    acquiring functional data of the at least one anatomical structure in a second field-of-view using a nuclear imaging system, the second field-of-view being smaller than the first field-of-view;
    reconstructing the structural data and the functional data into a structural image and an attenuation corrected first functional image, respectively;
    extracting, from the structural image, a map including at least one portion of the structural image excluded from the second field-of-view and included in the first field-of-view;
    extrapolating functional image values from the attenuation corrected first functional image to the at least one portion excluded from the second field-of-view and included in the first field-of-view to generate an extended field-of-view image representation; and
    reconstructing the extended field of view image representation corrected for at least one of spill-over and backscatter artifacts which originate outside of the second field-of-view based on the at least one portion excluded from the second field-of-view and included in the first field-of-view with extrapolated functional image values to generate an enhanced functional image.

8. The method according to claim 7, wherein the first field-of-view encompasses the second field-of-view.

9. The method according to claim 8, further including:
    generating an attenuation map based on the structural image; and reconstructing the functional data using the attenuation map to generate the attenuation corrected functional image.

10. The method according to claim 7, wherein at least one organ has a first portion disposed partially in the first field-of-view outside of the second field-of-view and a second portion disposed in the second field-of-view and further including:
identifying the second organ portion from the functional data;
identifying the first organ portion in the structural image; and
registering the first and second organ portions;
wherein extrapolating the functional image values includes extrapolating functional image values from the second organ portion to the first organ portion.

11. The method according to claim 7, further including:
generating a radiation activity model of the portion excluded from the second field-of-view and included in the first field-of-view and using the radiation activity model to correct for at least one of spill-over and backscatter.

12. The method according to claim 7, further including at least one of:
generating scatter correction data based on a scatter simulation derived from the extended field-of-view image representation;
or
generating spill-over correction data based on the extended field-of-view image representation; and
wherein reconstructing the extended field of view image representation includes using the correction data to correct for at least one of spill-over and backscatter artifacts.

13. The method according to claim 7, wherein acquiring the structural data includes:
performing a surview scan with a CT imaging system.

14. A non-transitory computer readable medium carrying a computer program which controls a processor to perform the method of claim 7.

15. A combined imaging system comprising:
a first imaging system configured to acquires structural data of at least one anatomical structure in a first field of view;
a nuclear imaging system configured to acquires-functional data of the at least one anatomical structure in a second field-of-view, the second field-of-view being smaller than the first field-of-view;
one or more processors configured to:
reconstruct the acquired structural data from the first imaging system into a first imaging system image representation;
extract from the first imaging system image representation a first map including at least a portion of at least one anatomical structure excluded from the second field-of-view and included in the first field-of-view;
generate an attenuation map based on the first imaging system image representation;
reconstruct the functional data into an attenuation corrected functional image representation using the attenuation map;
align, register, or fuse the attenuation corrected functional image representation and the first map and assign nuclear image values based on nuclear image values of the attenuation corrected functional image representation to the at least a portion of at least one anatomical structure excluded from the second field-of-view and included in the first field-of-view to generate an extended field-of-view functional image representation; and
reconstruct the extended field-of-view functional image representation being corrected for at least one of spill-over and backscatter artifacts based on the structural data acquired by the first imaging system.

16. An imaging system comprising:
at least one processor configured to:
generate a first system image representation and an attenuation map from structural data of at least one anatomical structure acquired in a first field-of-view (FOV) by a first imaging system;
reconstruct an attenuation corrected nuclear image representation from functional data, acquired by a nuclear imaging system in a second FOV, of the at least one anatomical structure based on the attenuation map, the second FOV being smaller than the first FOV, wherein the first image representation includes at least one organ disposed partially inside the second FOV and partially outside the second FOV;
extract from the first system image representation an anatomy map including a portion of the at least one organ disposed outside of the second FOV;
align, register, or fuse the attenuation corrected nuclear image representation and the anatomy map and extrapolate nuclear image intensity values to at least the portion of the at least one organ disposed outside of the second FOV based on nuclear image intensity values of a portion of the organ included in the second FOV to generate an extended FOV image representation; and
reconstruct the extended FOV image representation into a corrected nuclear image representation; and
a display connected with the at least one processor configured to display at least the corrected nuclear image representation.

17. The imaging system according to claim 16, wherein in reconstructing the extended FOV image representation into a corrected nuclear image representation, the at least one processor is configured to:
model radiation activity in the portion of the at least one organ disposed outside of the second FOV; and
performing spill-over correction based on the radiation activity model.

18. The imaging system according to claim 16, wherein in reconstructing the extended FOV image representation into a corrected nuclear image representation, the at least one processor is further configured to:
model radiation scatter attributable to radiation from the portion of the at least one organ disposed outside of the second FOV; and
perform scatter correction based on the scatter model.

19. The imaging system according to claim 16, wherein the at least one processor is further configured to:
correlate the portion of the at least one organ disposed outside of the second FOV with a model of the at least one organ.

* * * * *